United States Patent

Barreau et al.

[11] Patent Number: 4,769,366
[45] Date of Patent: Sep. 6, 1988

[54] NOVEL 1,3-DISUBSTITUTED PYRROLO[1,2-A]AZEPINONE DERIVATIVES HAVING ANTI-PSYCHOTIC ACTIVITY AND PHARMACEUTICAL COMPOSITIONS CONTAINING THEM

[75] Inventors: Michel Barreau, Montgeron; Marie-Therese Comte, Cachan; Daniel Farge, Thiais; Jean-Luc Malleron, Les Ulis; Gerard Ponsinet, Sucy en Brie; Gerard Roussel, Soisy sur Seine, all of France

[73] Assignee: Rhone-Poulenc Sante, Courbevoie, France

[21] Appl. No.: 839,101

[22] Filed: Mar. 13, 1986

[30] Foreign Application Priority Data

Mar. 15, 1985 [FR] France ............................. 85 03840

[51] Int. Cl.$^4$ .................. A61K 31/395; C07D 223/00
[52] U.S. Cl. ..................................... 514/214; 540/593; 540/575
[58] Field of Search ............... 540/593, 598, 575; 514/214

[56] References Cited
PUBLICATIONS
Dhimane et al., CA 103-37322c.

Primary Examiner—Donald G. Daus
Assistant Examiner—Cecilia Shen
Attorney, Agent, or Firm—Stevens, Davis, Miller & Mosher

[57] ABSTRACT

Pyrrolo[1,2-a]azepinone derivatives of formula:

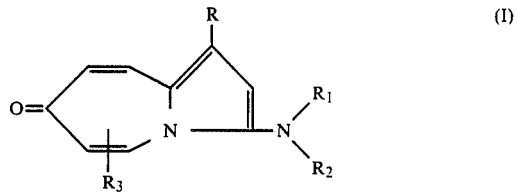

in which $R_3$ is H or halogen and
either (A) R is benzyl or phenylthio in which the phenyls are optionally substituted by one or more halogens or hydroxy, alkyl, alkyloxy or alkylthio radicals, $R_1$ and $R_2$, which may be identical or different, denote alkyl optionally substituted by dialkylamino in which the alkyls are optionally joined to form a 1-pyrrolidinyl, piperidino, morpholino or 1-piperazinyl ring substituted by alkyl, or alternatively $R_1$ and $R_2$ form a heterocyclic ring chosen from pyrrolidine, piperidine, morpholine and piperazine, substituted by alkyl, alkenyl (2 to 4 C), benzyl or phenethyl optionally substituted by halogen, alkyl, alkyloxy, alkylthio, $CF_3$, COOH, carboxyalkyl, alkyloxycarbonyl, alkyloxycarbonylalkyl, hydroxyalkyl, or alkylcarbonyloxyalkyl in which the alkylcarbonyl has 2 to 18 C, or (B) R is phenyl optionally substituted with one or more halogens or hydroxy, alkyl, alkyloxy or alkylthio radicals and $R_1$ and $R_2$ together form a piperazine or homopiperazine ring substituted by hydroxyalkyl (2 to 4 C), alkenyl (2 to 4 C), alkynyl (2 to 4 C), benzyl or phenethyl optionally substituted by halogen, alkyl, alkyloxy, alkylthio, CN, $CF_3$, COOH, carboxyalkyl, alkyloxycarbonyl, alkyloxycarbonylalkyl, hydroxyalkyl, or alkylcarbonyloxyalkyl in which the alkylcarbonyl has 2 to 18 C, the said alkyls containing, except where otherwise stated, 1 to 4 C in a straight or branched chain, and the pharmaceutically acceptable salts thereof, are useful as antipsychotics.

17 Claims, No Drawings

NOVEL 1,3-DISUBSTITUTED PYRROLO[1,2-A]AZEPINONE DERIVATIVES HAVING ANTI-PSYCHOTIC ACTIVITY AND PHARMACEUTICAL COMPOSITIONS CONTAINING THEM

The present invention provides new pyrrolo[1,2-a]azepinones of the formula:

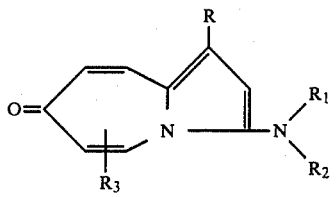

in which $R_3$ denotes hydrogen or halogen and either (A) R denotes benzyl or phenylthio in each of which the phenyl is unsubstituted or substituted by one or more halogen atoms or hydroxy, alkyl, alkyloxy or alkylthio radicals.

and $R_1$ and $R_2$, which may be identical or different, each denote alkyl which is unsubstituted or substituted by dialkylamino in which the alkyls are separate or are joined to form, with the nitrogen atom to which they are linked, 1-pyrrolidinyl, piperidino, morpholino or 1-piperazinyl substituted by alkyl, or alternatively $R_1$ and $R_2$ form, together with the nitrogen atom to which they are linked, 1-pyrrolidinyl, piperidino, morpholino or 1-piperazinyl substituted by alkyl, alkenyl of 2 to 4 carbon atoms, benzyl or phenethyl, the phenyl portions of the said benzyl or phenethyl being unsubstituted or substituted by halogen, alkyl, alkyloxy, alkylthio, trifluoromethyl, carboxy, carboxyalkyl, alkyloxycarbonyl, alkyloxycarbonylalkyl, hydroxyalkyl, or alkylcarbonyloxyalkyl in which the alkylcarbonyl portion contains 2 to 18 carbon atoms in a straight or branched chain, or (B) R denotes phenyl or phenyl substituted by one or more halogen atoms or hydroxy, alkyl, alkyloxy or alkylthio radicals, and $R_1$ and $R_2$ form, together with the nitrogen atom to which they are linked, a piperazino or homopiperazino ring substituted by hydroxyalkyl in which the alkyl contains 2 to 4 carbon atoms, alkenyl of 2 to 4 carbon atoms, alkynyl of 2 to 4 carbon atoms, or a benzyl or phenethyl radical in which the phenyl portion is unsubstituted or substituted by halogen, alkyl, alkyloxy, alkylthio, cyano, trifluoromethyl, carboxy, carboxyalkyl, alkyloxycarbonyl, alkyloxycarbonylalkyl, hydroxyalkyl, or alkylcarbonyloxyalkyl in which the alkylcarbonyl portion contains 2 to 18 carbon atoms in a straight or branched chain.

the aforesaid alkyl radicals and alkyl portions containing, except where otherwise stated, 1 to 4 carbon atoms each in a straight or branched chain, the substitution of piperazino or homopiperazino ring being in the 4-position on the nitrogen atom and the pharamaceutically acceptable salts thereof.

The invention further provides a process for preparing a pyrrolo[1,2-a]azepinone of the formula (I) in which $R_3$ denotes hydrogen or halogen, and either (A) R denotes benzyl or phenylthio in each of which the phenyl is unsubstituted or substituted by one or more halogen atoms or hydroxy, alkyl, alkyloxy or alkylthio radicals, and $R_1$ and $R_2$, which may be identical or different, each denote alkyl which is unsubstituted or substituted by dialkylamino in which the alkyls are separate or are joined to form, with the nitrogen atom to which they are linked, 1-pyrrolidinyl, piperidino, morpholino or 1-piperazinyl substituted by alkyl, or alternatively $R_1$ and $R_2$ form, together with the nitrogen atom to which they are linked, 1-pyrrolidinyl, piperidino, morpholino or 1-piperazinyl substituted by alkyl, alkenyl of 2 to 4 carbon atoms, benzyl or phenethyl, the phenyl portions of the said benzyl or phenethyl being unsubstituted or substituted by halogen, alkyl, alkyloxy, alkylthio, trifluoromethyl, carboxy, carboxyalkyl, alkyloxycarbonyl, alkyloxycarbonylalkyl, hydroxyalkyl, or alkylcarbonyloxyalkyl in which the alkylcarbonyl portion contains 2 to 18 carbon atoms in a straight or branched chain, or (B) R denotes phenyl or phenyl substituted by one or more halogen atoms or hydroxy, alkyl, alkyloxy or alkylthio radicals, and $R_1$ and $R_2$ form, together with the nitrogen atom to which they are linked, a piperazino or homopiperazino ring substituted by alkenyl of 2 to 4 carbon atoms, or a benzyl or phenethyl radical in which the phenyl portion is unsubstituted or substituted by halogen, alkyl, alkyloxy, alkylthio, trifluoromethyl, carboxy, carboxyalkyl, alkyloxycarbonyl, alkyloxycarbonylalkyl, hydroxyalkyl, or alkylcarbonyloxyalkyl in which the alkylcarbonyl portion contains 2 to 18 carbon atoms in a straight or branched chain, the aforesaid alkyl radicals and alkyl portions containing, except where otherwise stated, 1 to 4 carbon atoms each in a straight or branched chain, and the pharmaceutically acceptable salts thereof, which comprises rearranging a compound of the formula:

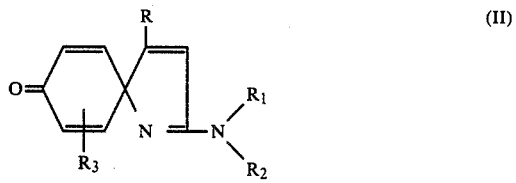

in which the symbols R and $R_3$ are defined as above and $R_1$ and $R_2$ are defined as above except that they do not form, with the nitrogen atom to which they are linked, a piperazino or homopiperazino ring substituted by a benzyl or phenethyl radical in which the phenyl is substituted by carboxy, carboxyalkyl, hydroxyalkyl or alkylcarbonyloxyalkyl in which the alkylcarbonyl contains 2 to 18 carbon atoms in a straight or branched chain, to produce a compound of formula (I) in which the symbols are as defined above, except that $R_1$ and $R_2$ do not form, with the nitrogen atom to which they are linked, a piperazino or homopiperazino ring substituted by a benzyl or phenethyl radical in which the phenyl is substituted by carboxy, carboxyalkyl, hydroxyalkyl, or alkylcarbonyloxyalkyl in which the alkylcarbonyl contains 2 to 18 carbon atoms in a straight or branched chain:

isolating the product obtained and then, if a product of formula (I) in which R and $R_3$ are as defined above and $R_1$ and $R_2$ form, with the nitrogen atom to which they are linked, a piperazino or homopiperazino ring substituted by a benzyl or phenethyl radical in which the phenyl is substituted by carboxy, carboxyalkyl or hydroxyalkyl is required, converting the corresponding product of formula (I), in which R and $R_3$ are as defined above and $R_1$ and $R_2$ form, with the nitrogen atom to which they are linked, a piperazino or homopiperazino ring substituted by a benzyl or phenethyl radical in which the phenyl is substituted by alkyloxycarbonyl or alkyloxycarbonylalkyl, into a corresponding acid or alcohol, and if required, acylating the alcohol obtained to produce a product of general formula (I) in which R and $R_3$ are as defined above and $R_1$ and $R_2$, form with the nitrogen atom to which they are linked, a piperazino or homopiperazino ring substituted by a benzyl or phenethyl radical in which the phenyl is substituted by alkylcarbonyloxyalkyl in which the alkylcarbonyl contains 2 to 18 carbon atoms in a straight or branched chain;

and isolating the product and if required converting it into a pharmaceutically acceptable salt.

This process is suitable for preparing the compounds of formula (I) as defined above, with the exception of those in which $R_1$ and $R_2$ form, together with the nitrogen atom to which they are linked, a piperazino or homopiperazino ring substituted by hydroxyalkyl in which the alkyl contains 2 to 4 carbon atoms, alkynyl of 2 to 4 carbon atoms, or a benzyl or phenethyl radical substituted by cyano.

The rearrangement of the compound of formula (II) is generally accomplished by heating it to a temperature of between 190° and 250° C. without a solvent, or in an organic solvent having a high boiling point such as 1,2,4-trichlorobenzene.

The products of formula (II) in which R and $R_3$ are as defined above, except that they do not form, with the nitrogen atom to which they are linked, a piperazino or homopiperazino ring substituted by hydroxyalkyl of 2 to 4 carbon atoms, alkynyl of 2 to 4 carbon atoms, or a benzyl or phenethyl radical substituted by cyano, carboxy, carboxyalkyl, hydroxyalkyl or alkylcarbonyloxyalkyl in which the alkylcarbonyl contains 2 to 18 carbon atoms in a straight or branched chain, can be obtained by cyclization of a compound of formula:

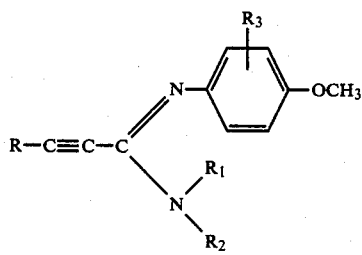

(III)

in which the symbols R and $R_3$ are as defined above and $R_1$ and $R_2$ are as defined above except that they do not form, with the nitrogen atom to which they are linked, a piperazino or homopiperazino ring substituted by hydroxyalkyl in which the alkyl contains 2 to 4 carbon atoms, alkynyl of 2 to 4 carbon atoms, or a benzyl or phenethyl radical substituted by cyano, carboxy, carboxyalkyl, hydroxyalkyl, or alkylcarbonyloxyalkyl in which the alkylcarbonyl portion contains 2 to 18 carbon atoms in a straight or branched chain.

The cyclization is generally accomplished with a strong mineral acid such as concentrated sulphuric acid, optionally in a solvent such as acetic acid or chloroform, or using a mixture of phosphoric anhydride and methanesulphonic acid (1:9 by volume) at a temperature of 0° to 20° C., or with polyphosphoric acid at a temperature of between 100° and 120° C.

The compounds of formula (III) can be prepared by the action of an organometallic derivative of formula:

(IV)

in which R is as defined above, on a compound of formula:

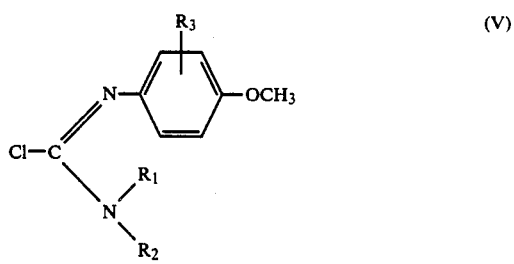

(V)

in which $R_3$ is as defined above and $R_1$ and $R_2$ are as defined above except that they do not form, with the nitrogen atom to which they are linked, a piperazino or homopiperazino ring substituted by hydroxyalkyl in which the alkyl portion contains 2 to 4 carbon atoms, alkynyl of 2 to 4 carbon atoms, or a benzyl or phenethyl radical substituted by cyano, carboxy, carboxyalkyl, hydroxyalkyl or alkylcarbonyloxyalkyl in which the alkylcarbonyl portion contains 2 to 18 carbon atoms in a straight or branched chain.

The reaction is generally performed in an organic solvent, e.g. an ether such as tetrahydrofuran or a hydrocarbon such as hexane or a mixture of these solvents, at a temperature of between −70° and +20° C.

The compounds of formula (V) can be prepared by the action of the N-dichloromethylene-p-anisidine of formula:

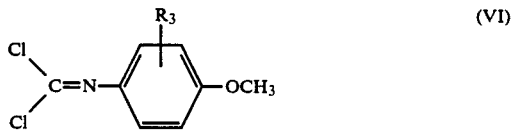

(VI)

in which $R_3$ is defined as above, on an amine of formula:

(VII)

in which $R_1$ and $R_2$ are as defined except that they do not form, with the nitrogen atom to which they are linked, a piperazino or homopiperazino ring substituted by hydroxyalkyl in which the alkyl portion contains 2 to 4 carbon atoms, alkynyl of 2 to 4 carbon atoms, or a benzyl or phenethyl radical substituted by cyano, carboxy, carboxyalkyl, hydroxyalkyl or alkylcarbonyloxyalkyl in which the alkylcarbonyl portion contains 2 to 18 carbon atoms in a straight or branched chain.

The reaction is generally performed in a solvent, e.g. an ether such as tetrahydrofuran, at a temperature in the region of 20° C.

In practice, it is not necessary to isolate the product of formula (V) in order to prepare the compounds of formula (III). After the compound of formula (VI) has been reacted with the compound of formula (VII), as described above, it is sufficient to add the organometallic derivative of formula (IV) in sufficient quantity, either directly to the reaction mixture or, where appropriate and if so desired, after filtering off the amine hydrochloride formed.

The compounds of formula (VI) can be prepared by application or adaptation of one of the methods mentioned by E. Kühle, Ang. Chem. Int. Ed., 1, 647 (1962).

The invention also provides a process for preparing a pyrrolo[1,2-a]azepinone of formula (I)
in which $R_3$ denotes a hydrogen or halogen atom, and R denotes phenyl or phenyl substituted by one or more halogen atoms or hydroxy, alkyl, alkyloxy or alkylthio radicals.
and $R_1$ and $R_2$ form, together with the nitrogen atom to which they are linked, a piperazino or homopiperazino ring
substituted by hydroxyalkyl in which the alkyl contains 2 to 4 carbon atoms, alkenyl of 2 to 4 carbon atoms, alkynyl of 2 to 4 carbon atoms, or a benzyl or phenethyl radical in which the phenyl portion is unsubstituted or substituted by halogen, alkyl, alkyloxy, alkylthio, cyano, trifluoromethyl, carboxy, carboxyalkyl, alkyloxycarbonyl, alkyloxycarbonylalkyl, hydroxyalkyl, or alkylcarbonyloxyalkyl in which the alkylcarbonyl portion contains 2 to 18 carbon atoms in a straight or branched chain, the aforesaid alkyl radicals and alkyl portions containing, except where otherwise stated, 1 to 4 carbon atoms each in a straight or branched chain,
and the pharmaceutically acceptable salts thereof, which comprises reacting a compound of formula:

$$R_4X \qquad (VIII)$$

in which $R_4$ denotes hydroxyalkyl in which the alkyl contains 2 to 4 carbon atoms, alkenyl of 2 to 4 carbon atoms, alkynyl of 2 to 4 carbon atoms, or a benzyl or phenethyl radical in which the phenyl portion is unsubstituted or substituted by halogen, alkyl, alkyloxy, alkylthio, cyano, trifluoromethyl, carboxy, carboxyalkyl, alkyloxycarbonyl, alkyloxycarbonylalkyl, hydroxyalkyl or alkylcarbonyloxyalkyl in which the alkylcarbonyl portion contains 2 to 18 carbon atoms in a straight or branched chain, and X denotes a halogen atom, e.g. the chlorine, bromine or iodine atom, with a compound of the formula:

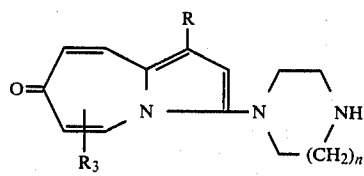
(IX)

in which n is 1 to 2, and R and $R_3$ are as defined above, isolating the product obtained and if required converting it into a pharmaceutically acceptable salt.

This process is applicable to the preparation of compounds of formula (I) in which $R_3$ is as defined above and the other symbols are as defined above at (B).

The reaction is generally performed in an organic solvent, e.g. a chlorinated solvent such as chloroform, at a temperature of between 20° C. and the refluxing temperature of the reaction mixture, in the presence of an acceptor for acid such as 4-dimethylaminopyridine.

The compounds of formula (IX) can be prepared by deallylation of a compound of formula (I) in which $R_1$ and $R_2$ form, together with the nitrogen atom to which they are linked, a piperazino or homopiperazino ring substituted by allyl and the other symbols are as defined above, i.e. a compound of formula:

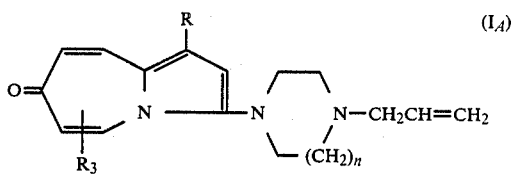

The reaction is generally performed in an aqueous organic solvent such as a mixture of dioxane and water at a temperature of between 50° C. and the refluxing temperature of the reaction mixture, in the presence of rhodium trichloride or a catalyst derived from transition metals which are known for their ability to deallylate amines, such as e.g. those which are described or mentioned by D. Picq, M. Cottin, D. Anker and H. Pacheco, Tetr. Letters, 1399 (1983).

The products of general formula ($I_A$) can be prepared by rearrangement of a product of general formula (II), as described above.

It is obvious for those skilled in the art that, depending on the nature of the radicals bound to the molecule, it may be necessary to block a particular functional group before carrying out one of the processes of the invention. Thus, when $R_1$ and $R_2$ form, with the nitrogen atom to which they are linked, a piperazino or homopiperazino ring substituted by hydroxyalkyl, the alcohol group can be protected in the form of a tetrahydropyranyloxy radical which is introduced at the stage of the synthesis which is judged to be most propitious. Unblocking is then accomplished in known manner, e.g. by the action of an aqueous mineral acid.

The compounds of formula (I) can be purified by the customary known methods, e.g. by crystallization, chromatography, successive extractions in acidic and basic medium or salt formation and recrystallization of these salts.

The compounds of formula (I) can be converted into addition salts with acids, by the action of an acid in an organic solvent such as an alcohol, a ketone, an ether or a chlorinated solvent. The salt formed precipitates, where appropriate after concentration of the solution thereof; it is separated by filtration or decantation.

When the products of formula (I) possess a carboxylic acid group in their molecule, they can be converted into metal salts or into addition salts with amines, by any known method.

The compounds of formula (I) and their pharmaceutically acceptable salts possess advantageous pharmacological properties which make them useful as antipsychotics. They have been shown to be active in rats at doses of between 1 and 80 mg/kg administered orally in the test of inhibition of yawning induced by a low dose of apomorphine according to I. Dubuc, P. Protais, O. Colboc and J. Costentin, Neuropharmacology, Vol. 21, P. 1203–1206 (1982).

Of special value are the compounds of formula (I) in which $R_3$ denotes a hydrogen or halogen atom and
(A) either R denotes a phenylthio radical and $R_1$ and $R_2$ form, together with the nitrogen atom to which they are linked, a piperazino ring substituted by alkyl, alkenyl of 2 to 4 carbon atoms, or a benzyl radical in which the phenyl portion is unsubstituted or substituted by a halogen atom or an alkyl, alkyloxy, alkylthio, trifluoromethyl, carboxy or carboxyalkyl radical,
(B) or R denotes phenyl or phenyl substituted by one or more halogen atoms or hydroxy, alkyl, alkyloxy or alkylthio radicals and $R_1$ and $R_2$ form, together with the nitrogen atom to which they are linked, a piperazino or homopiperazino ring substituted by hydroxyalkyl in which the alkyl contains 2 to 4 carbon atoms, alkenyl of 2 to 4 carbon atoms, alkynyl of 2 to 4 carbon atoms, or a benzyl or phenethyl radical in which the phenyl portion is unsubstituted or substituted by halogen, alkyl, cyano, trifluoromethyl, carboxy, carboxyalkyl, alkyloxycarbonyl, hydroxyalkyl or alkylcarbonyloxyalkyl in which the alkylcarbonyl portion contains 2 to 18 carbon atoms in a straight or branched chain.

Of more special value are the compounds of formula (I) in which $R_3$ denotes a hydrogen or halogen atom and
either (A) R denotes phenylthio and $R_1$ and $R_2$ form, together with the nitrogen atom to which they are linked, a 1-piperazinyl ring substituted by alkyl or by alkenyl of 2 to 4 carbon atoms,
or (B) R denotes phenyl or phenyl substituted by hydroxy, alkyl or alkyloxy and $R_1$ and $R_2$ form, together with the nitrogen atom to which they are linked, a piperazino or homopiperazino ring substituted by hydroxyalkyl in which the alkyl portion contains 2 to 4 carbon atoms, alkenyl of 2 to 4 carbon atoms, alkynyl of 2 to 4 carbon atoms, or benzyl in which the phenyl portion is unsubstituted or substituted by halogen, alkyl, cyano, trifluoromethyl, carboxy or alkyloxycarbonyl.

Of most especial value are the following products of formula (I):

3-[4-(4-methylbenzyl)-1-piperazinyl]-1-phenyl-7H-pyrrolo[1,2-a]azepin-7-one
1-(4-hydroxyphenyl)-3-[4-(4-methylbenzyl)-1-piperazinyl]-7H-pyrrolo[1,2-a]azepin-7-one
3-[4-(4-methylbenzyl)-1-piperazinyl]-1-(4-methoxyphenyl)-7H-pyrrolo[1,2-a]azepin-7-one
3-(4-benzyl-1-piperazinyl)-1-(4-hydroxyphenyl)-7H-pyrrolo[1,2-a]azepin-7-one
3-(4-benzyl-1-piperazinyl)-1-(4-methoxyphenyl)-7H-pyrrolo[1,2-a]azepin-7-one
3-[4-(4-fluorobenzyl)-1-piperazinyl]-1-phenyl-7H-pyrrolo[1,2-a]azepin-7-one
3-(4-benzyl-1-piperazinyl)-1-phenyl-7H-pyrrolo[1,2-a]azepin-7-one
3-[4-(3-trifluoromethylbenzyl)-1-piperazinyl]-1-phenyl-7H-pyrrolo[1,2-a]azepin-7-one
3-[4-(4-methylbenzyl)-1-piperazinyl]-1-(2-methoxyphenyl)-7H-pyrrolo[1,2-a]azepin-7-one
3-(4-methyl-1-piperazinyl)-1-phenylthio-7H-pyrrolo[1,2-a]azepin-7-one
3-(4-allyl-1-piperazinyl)-1-phenylthio-7H-pyrrolo[1,2-a]azepin-7-one
3-[4-(4-carboxybenzyl)-1-piperazinyl]-1-phenyl-7H-pyrrolo[1,2-a]azepin-7-one The new products of general formula (I) possess low toxicity. Their $LD_{50}$ is between 100 and 900 mg/kg administered orally in mice.

As examples of pharmaceutically acceptable salts, there may be mentioned the addition salts with mineral acids (such as hydrochlorides, sulphates, nitrates, phosphates) or organic acids (such as acetates, propionates, succinates, benzoates, fumarates, maleates, methanesulphonates, isethionates, theophyllineacetates, salicylates, phenolphthalinates, methylenebis-$\beta$-oxynaphthoates) or substitution derivatives of these compounds, or alternatively the salts with alkali metals such as sodium, potassium or lithium salts or addition salts with bases such as ammonium, ethanolamine or lysine salts.

The examples which follow, which are given without implied limitation, show how the invention may be put into practice.

EXAMPLE 1

2-(4-Allyl-1-piperazinyl)-4-phenyl-1-azaspiro[4.5]deca-1,3,6,9-tetraen-8-one (40 g) is heated for 10 minutes to a temperature of about 220° C. After being cooled to a temperature of about 20° C., the residue is dissolved in methylene chloride (500 cc) and poured into silica (1 kg) contained in a column 6.5 cm in diameter. Successive elutions are performed with pure methylene chloride (1 liter), a mixture of methylene chloride and ethyl acetate (90:10 by volume) (1 liter) and a mixture of methylene chloride and ethyl acetate (80:20 by volume) (1 liter); the corresponding eluates are discarded. Elution is then performed with a mixture of methylene chloride and ethyl acetate (70:30 by volume) (3 liters) and the corresponding eluate is evaporated to dryness under reduced pressure (20 mm Hg; 2.7 kPa) at 40° C. After recrystallization of the residue in acetonitrile (200 cc), 3-(4-allyl-1-piperazinyl)-1-phenyl-7H-pyrrolo[1,2-a]azepin-7-one (28 g), m.p. 125° C., is obtained.

2-(4-Allyl-1-piperazinyl)-4-phenyl-1-azaspiro[4.5]deca-1,3,6,9-tetraen-8-one can be prepared in the following manner: concentrated sulphuric acid (200 cc) is added in the course of 10 minutes at a temperature of about 0° C. to 3-(4-allyl-1-piperazinyl)-3-(4-methoxyphenylimino)-1-phenyl-1-propyne (49.3 g) and the reaction mixture is stirred for 12 hours at a temperature of about 20° C. The reaction mixture is then poured in the course of 10 minutes onto crushed ice (500 g). 10N sodium hydroxide (800 cc) is then added with stirring, followed by distilled water (200 cc). The aqueous solution is washed with methylene chloride (3×500 cc). The organic extracts are combined, washed with distilled water (2×200 cc), dried over anhydrous magnesium sulphate, filtered and evaporated to dryness under reduced pressure (20 mm Hg; 2.7 kPa) at 40° C. The residue thereby obtained is dissolved in methylene chloride (1 liter) and the solution is poured into silica (1 kg) contained in a column 6.2 cm in diameter. Elution is performed with a mixture of ethyl acetate and methanol (95:5 by volume) (1 liter) and then a mixture of ethyl acetate and methanol (90:10 by volume) (1 liter); these eluates are rejected. Elution is then performed with a mixture of ethyl acetate and methanol (80:20 by volume) (2 liters; the corresponding eluate is evaporated to dryness under reduced pressure (20 mm Hg; 2.7 kPa) at 40° C. After recrystallization of the residue in ethyl acetate (100 cc), 2-(4-allyl-1-piperazinyl)-4-phenyl-1-azaspiro[4.5]deca-1,3,6,9-tetraen-8-one (9.8 g), m.p. 171° C., is obtained.

3-(4-Allyl-1-piperazinyl)-3-(4-methoxyphenylimino)-1-phenyl-1-propyne can be prepared in the following manner: to a solution of N-(dichloromethylene)-p-anisidine (59 g) in ethyl ether (600 cc), a solution of 1-allylpiperazine (72 g) in tetrahydrofuran (450 cc) is added at a temperature of about 20° C. and in the course of 20 minutes, and stirring is continued for a further 30 minutes at a temperature of about 20° C. The precipitate which is formed is separated by filtration. The solution thereby obtained is added in the course of 3 minutes, at a temperature of about −65° C., to a solution of phenylethynyllithium in tetrahydrofuran (600 cc), obtained by reacting phenylacetylene (30.6 g) dissolved in tetrahydrofuran (600 cc) with a 1.6M solution (187 cc) of n-butyllithium in hexane at a temperature of about 20° C. The reaction mixture is allowed to warm up to a temperature of about 20° C. and then poured onto crushed ice (500 g). The aqueous phase is decanted and washed with ethyl ether (3×500 cc). The ether fractions are combined, washed with distilled water (250 cc), dried over anhydrous magnesium sulphate, filtered and then evaporated to dryness under reduced pressure (20 mm Hg; 2.7 kPa) at 40° C. The residue obtained is dissolved in methylene chloride (200 cc) and the solution is poured into silica (2 kg) contained in a column 8 cm in diameter. Elution is performed with mixtures of methylene chloride and ethyl acetate (4×1 liter containing, respectively, 10%, 20%, 30% and 40% of ethyl acetate); the corresponding eluates are rejected. Elution is then performed with a mixture of methylene chloride and ethyl acetate (50:50 by volume) (3 liters); the corresponding eluate is evaporated to dryness under reduced pressure (20 mm Hg; 2.7 kPa) at 40° C. The residue obtained is dissolved in boiling acetonitrile (175 cc); maleic acid (35 g) dissolved in boiling acetonitrile (350 cc) is added to the solution. After the mixture is cooled to a temperature of about 20° C., the precipitate formed is separated by filtration. After recrystallization in acetonitrile (550 cc), 3-(4-allyl-1-piperazinyl)-3-(4-methoxyphenylimino)-1-phenyl-1-propyne dimaleate (58.3 g), m.p. 180° C., is thereby obtained.

N-Dichloromethylene-p-anisidine can be prepared according to the method described by G. M. Dyson and T. Harrington, J. Chem. Soc., 191, (1940).

EXAMPLE 2

A solution of 1-phenyl-3-(1-piperazinyl)-7H-pyrrolo[1,2-a]azepin-7-one (3 g), α-chloro-para-xylene (2.5 g) and 4-dimethylaminopyridine (1.46 g) in chloroform (100 cc) is heated for 48 hours to a temperature of about 60° C. After evaporation to dryness under reduced pressure (20 mm Hg; 2.7 kPa) at 40° C., the residue obtained is redissolved in methylene chloride (250 cc) and the solution obtained is poured into silica (100 g) contained in a column 3 cm in diameter. Elution is performed first with pure chloroform (1 liter) and then a mixture of chloroform and methanol (95:5 by volume) (1 liter); these eluates are rejected. Elution is then performed with a mixture of chloroform and methanol (90:10 by volume) (1 liter) and the corresponding eluate is evaporated to dryness under reduced pressure (20 mm Hg; 2.7 kPa) at 40° C. The corresponding residue is dissolved in boiling acetonitrile (10 cc). A solution of oxalic acid (0.6 g) in boiling ethanol (5 cc) is added dropwise. After the mixture is cooled to a temperature of about 20° C., the precipitate formed is separated by filtration. After recrystallization of the residue in a solution of ethanol (20 cc) and distilled water (10 cc), 3-[4-(4-methylbenzyl)-1-piperazinyl]-1-phenyl-7H-pyrrolo[1,2-a]azepin-7-one oxalate (1.2 g), m.p. 150° C. (with decomposition), is obtained.

1-Phenyl-3-(1-piperazinyl)-7H-pyrrolo[1,2-a]azepin-7-one can be prepared in the following manner: a solution of 3-(4-allyl-1-piperazinyl)-1-phenyl-7H-pyrrolo[1,2-a]azepin-7-one (60.8 g), rhodium trichloride (5.1 g) and 1,4-diazabicyclo[2.2.2]octane (DABCO) (9.9 g) in dioxane (2 liters) and distilled water (200 cc) is heated to a temperature of about 88° C. for 24 hours. After evaporation of the solvents under reduced pressure (20 mm Hg; 2.7 kPa) at 40° C., the white residue is redissolved in methylene chloride (2 liters) and the solution is poured into silica (1.5 kg) contained in a column 7.5 cm in diameter. Elution is performed first with chloroform (2 liters), then a mixture of chloroform and methanol (95:5 by volume) (2 liters), then a mixture of chloroform and methanol (90:10 by volume) (2 liters), and then a mixture of chloroform and methanol (85:15 by volume) (2 liters). The corresponding eluates are rejected. Elution is then performed with a mixture of chloroform and methanol (80:20 by volume) (4 liters), and the corresponding eluate is evaporated to dryness under reduced pressure (20 mm Hg; 2.7 kPa) at 40° C. 1-Phenyl-3-(1-piperazinyl)-7H-pyrrolo[1,2-a]azepin-7-one (36 g) is thereby obtained in the form of a brown cake which is used without further purification in the subsequent syntheses.

3-(4-Allyl-1-piperazinyl)-1-phenyl-7H-pyrrolo[1,2-a]azepin-7-one can be prepared as described in Example 1.

EXAMPLE 3

By working as in Example 2, but starting with 1-phenyl-3-(1-piperazinyl)-7H-pyrrolo[1,2-a]azepin-7-one (3.05 g), α-bromo-p-toluonitrile (2.35 g) and 4-dimethylaminopyridine (1.48 g) in solution in chloroform (80 cc), 3-[4-(4-cyanobenzyl)-1-piperazinyl]-1-phenyl-7H-pyrrolo[1,2-a]azepin-7-one (0.54 g), m.p. 196° C., is obtained after recrystallization in ethanol (25 cc).

EXAMPLE 4

2-(4-Benzyl-1-piperazinyl)-4-phenyl-1-azaspiro[4.5]deca-1,3,6,9-tetraen-8-one (14.6 g) is heated for 10 minutes to a temperature of about 200° C. After being cooled to a temperature of about 20° C., the residue obtained is dissolved in methylene chloride (500 cc) and the solution is poured into silica (300 g) contained in a column 4.2 cm in diameter. Elution is performed first with pure methylene chloride (4 liters); the corresponding eluate is rejected. Elution is then performed with a mixture of methylene chloride and methanol (90:10 by volume) (3 liters) and the eluate is evaporated to dryness under reduced pressure (20 mm Hg; 2.7 kPa) at 40° C. After recrystallization of the residue in acetonitrile (200 cc), 3-(4-benzyl-1-piperazinyl)-1-phenyl-7H-pyrrolo[1,2-a]azepin-7-one (10.5 g), m.p. 157° C., is obtained.

2-(4-Benzyl-1-piperazinyl)-4-phenyl-1-azaspiro[4.5]deca-1,3,6,9-tetraen-8-one can be prepared in the following manner: to concentrated sulphuric acid (110 cc) cooled to a temperature of about 0° C., 3-(4-benzyl-1-piperazinyl)-3-(4-methoxyphenylimino)-1-phenyl-1-propyne (35.5 g) is added with stirring and the mixture is stirred for 12 hours, the temperature being allowed to rise to about 20° C. The reaction mixture is then poured into ice-cold water (500 cc). 10N aqueous sodium hydroxide solution (400 cc) is added and the mixture is washed 3 times with methylene chloride (1500 cc in total). The organic phases are combined, dried over sodium sulphate, filtered and evaporated to dryness under reduced pressure (20 mm Hg; 2.7 kPa) at 40° C. The residue is dissolved in methylene chloride (1000 cc) and the solution is poured into silica (600 g) contained in a column 5.4 cm in diameter. Elution is performed first with ethyl acetate (5 liters); this eluate is rejected. Elution is then performed with a mixture of ethyl acetate and methanol (90:10 by volume) (5 liters) and the corresponding eluate is evaporated to dryness under reduced pressure (20 mm Hg; 2.7 kPa) at 40° C. After recrystallization in ethanol (250 cc), 2-(4-benzyl-1-piperazinyl)-4-phenyl-1-azaspiro[4.5]deca-1,3,6,9-tetraen-8-one (20 g), m.p. 190° C., is obtained.

3-(4-Benzyl-1-piperazinyl)-3-(4-methoxyphenylimino)-1-phenyl-1-propyne can be prepared in the following manner: to a solution of N-dichloromethylene-p-anisidine (51 g) dissolved in ethyl ether (500 cc), a solution of 1-benzylpiperazine (97 g) in tetrahydrofuran (300 cc) is added at a temperature of about 20° C. and in the course of 20 minutes, and stirring is continued for a further 30 minutes at a temperature of about 20° C. The precipitate which is formed is separated by filtration. The solution thereby obtained is added in the course of 30 minutes at a temperature of about −65° C. to a solution of phenylethynyllithium in tetrahydrofuran (500 cc), obtained by reacting, at a temperature of about −20° C., a solution of phenylacetylene (28 g) in tetrahydrofuran (500 cc) with a 1.6M solution (172 cc) of n-butyllithium in hexane. The reaction mixture is allowed to warm to a temperature of about 20° C. and then poured onto crushed ice (500 g). The aqueous phase is decanted and washed 3 times with ethyl ether (1500 cc in total). The ether fractions are combined, washed with distilled water (250 cc), dried over anhydrous magnesium sulphate, filtered and evaporated to dryness under reduced pressure (20 mm Hg; 2.7 kPa) at 40° C. The residue obtained is dissolved in methylene chloride (500 cc) and the solution is poured into silica (2 kg) contained in a column 8.0 cm in diameter. Elution is performed first with methylene chloride (3 liters); the corresponding eluate is rejected. Elution is then performed with methylene chloride (5 liters) and the corresponding eluate is evaporated to dryness under reduced pressure (20 mm Hg; 2.7 kPa) at 40° C. 3-(4-benzyl-1-piperazinyl)-3-(4-methoxyphenylimino)-1-phenyl-1-propyne (53 g), m.p. 104° C., is thereby obtained.

EXAMPLE 5

2-[4-(4-Fluorobenzyl)-1-piperazinyl]-4-phenyl-1-azaspiro[4.5]deca-1,3,6,9-tetraen-8-one (21.4 g) in 1,2,4-trichlorobenzene (500 cc) is heated for 4 hours to a temperature of about 210° C. After evaporation to dryness under reduced pressure (1 mm Hg; 0.13 kPa) at 40° C., the residue obtained is dissolved in chloroform (500 cc) and the solution is poured into silica (400 g) contained in a column 4.7 cm in diameter. Elution is performed first with chloroform (1 liter) and then with a mixture of chloroform and methanol (99:1 by volume) (1 liter); the corresponding eluates are rejected. Elution is then performed with a mixture of chloroform and methanol (98:2 by volume) (2 liters) and the corresponding eluate is evaporated to dryness under reduced pressure (20 mm Hg; 2.7 kPa) at 40° C. After recrystallization of the residue in a solution of ethanol and dimethylformamide (85:15 by volume) (180 cc), 3-[4-(4-fluorobenzyl)-1-piperazinyl]-1-phenyl-7H-pyrrolo[1,2-a]azepin-7-one (10.5 g), m.p. 194° C., is obtained.

2-[4-(4-Fluorobenzyl)-1-piperazinyl]-4-phenyl-1-azaspiro[4.5]deca-1,3,6,9-tetraen-8-one can be prepared by working as in Example 4, but starting with 3-[4-(4-fluorobenzyl)-1-piperazinyl]-3-(4-methoxyphenylimino)-1-phenyl-1-propyne (5.8 g) and concentrated sulphuric acid (25 cc). After recrystallization in acetonitrile (30 cc), 2-[4-(4-fluorobenzyl)-1-piperazinyl]-4-phenyl-1-azaspiro[4.5]deca-1,3,6,9-tetraen-8-one (2.6 g), m.p. 188° C., is obtained.

3-[4-(4-Fluorobenzyl)-1-piperazinyl]-3-(4-methoxyphenylimino)-1-phenyl-1-propyne can be prepared by working as in Example 4, but starting with N-dichloromethylene-p-anisidine (20.4 g) dissolved in ethyl ether (150 cc), 4-(4-fluorobenzyl)piperazine (38.8 g) dissolved in tetrahydrofuran (150 cc) and a solution of phenylethynyllithium obtained by reacting phenylacetylene (11.2 g) dissolved in tetrahydrofuran (200 cc) with a 1.6M solution (68 cc) of n-butyllithium in hexane. After recrystallization in isopropyl ether (150 cc), 3-[4-(4-fluorobenzyl)-1-piperazinyl]-3-(4-methoxyphenylimino)-1-phenyl-1-propyne (23 g), m.p. 98° C., is obtained.

EXAMPLE 6

By working as in Example 5, but starting with 4-phenyl-2-[4-(3-trifluoromethylbenzyl)-1-piperazinyl]-1-azaspiro[4.5]deca-1,3,6,9-tetraen-8-one (8 g) and 1,2,4-trichlorobenzene (150 cc), 1-phenyl-3-[4-(3-trifluoromethylbenzyl)-1-piperazinyl]-7H-pyrrolo[1,2-a]azepin-7-one (2.5 g) m.p. 154° C., is obtained after recrystallization in ethanol (75 cc).

4-Phenyl-2-[4-(3-trifluoromethylbenzyl)-1-piperazinyl]-1-azaspiro[4.5]deca-1,3,6,9-tetraen-8-one can be prepared by working as in Example 4, but starting with 3-(4-methoxyphenylimino)-1-phenyl-3-[4-(3-trifluoromethylbenzyl)-1-piperazinyl]-1-propyne (6.8 g) and concentrated sulphuric acid (35 cc). After recrystallization in isopropyl ether (120 cc), 4-phenyl-2-[4-(3-trifluoromethylbenzyl)-1-piperazinyl]-1-azaspiro[4.5]deca-1,3,6,9-tetraen-8-one (2.3 g), m.p. 135° C., is obtained.

3-(4-Methoxyphenylimino)-1-phenyl-3-[4-(3-trifluoromethylbenzyl)-1-piperazinyl]-1-propyne can be prepared by working as in Example 4, but starting with N-dichloromethylene-p-anisidine (9.4 g) dissolved in ethyl ether (100 cc), 1-(3-trifluoromethylbenzyl)piperazine (22.5 g) dissolved in tetrahydrofuran (50 cc) and a solution of phenylethynyllithium obtained by reacting a phenylacetylene (5.1 g) dissolved in tetrahydrofuran (100 cc) with a 1.6M solution (31 cc) of n-butyllithium in hexane. The residue thereby obtained is dissolved in chloroform (250 cc) and the solution is poured into silica (400 g) contained in a column 4.7 cm in diameter. Elution is performed first with pure chloroform (1 liter), then a mixture of chloroform and methanol (99:1 by volume) (1 liter), and then a mixture of chloroform and methanol (98:2 by volume) (1 liter); the corresponding eluates are rejected. Elution is then performed with a mixture of chloroform and methanol (97.5:2.5 by volume) (2 liters), and the corresponding eluate is evaporated to dryness under reduced pressure (20 mm Hg; 2.7 kPa) at 40° C. The residue obtained is dissolved in boiling ethanol (200 cc). To this solution, maleic acid (7.2 g)

dissolved in boiling ethanol (150 cc) is added. After the mixture is cooled to a temperature of about 20° C., the precipitate formed is separated by filtration, washed with ethanol (40 cc) and then ethyl ether (50 cc). 3-(4-Methoxyphenylimino)-1-phenyl-3-[4-(3-trifluoromethylbenzyl)-1-piperazinyl]-1-propyne dimaleate (13.6 g), m.p. 175° C., is thereby obtained.

EXAMPLE 7

By working as in Example 5, but starting with 2-[4-(2-methylbenzyl)-1-piperazinyl]-4-phenyl-1-azaspiro[4.5-]deca-1,3,6,9-tetraen-8-one (5.8 g) and 1,2,4-trichlorobenzene (50 cc), 3-[4-(2-methylbenzyl)-1-piperazinyl]-1-phenyl-7H-pyrrolo[1,2-a]azepin-7-one (2.3 g), m.p. 133° C., is obtained after recrystallization in a mixture of isopropyl ether and ethyl acetate (50:50 by volume).

2-[4-(2-Methylbenzyl)-1-piperazinyl]-4-phenyl-1-azaspiro[4.5]deca-1,3,6,9-tetraen-8-one can be prepared in the following manner: 3-(4-methoxyphenylimino)-3-[4-(2-methylbenzyl)-1-piperazinyl]-1-phenyl-1-propyne maleate (14.2 g) is added in small portions in the course of 10 minutes to concentrated sulphuric acid (60 cc) at a temperature of about 0° C. The mixture is then stirred for 24 hours at a temperature of about 20° C. The reaction mixture is then poured onto crushed ice (200 g) and 10N aqueous sodium hydroxide solution (130 cc) is added. The aqueous solution is decanted and washed with chloroform (3×500 cc). The chloroform fractions are combined, dried over anhydrous sodium sulphate, filtered and evaporated to dryness under reduced pressure (20 mm Hg; 2.7 kPa) at 40° C. The residue thereby obtained is dissolved in chloroform (300 cc) and this solution is poured into silica (300 g) contained in a column 4.2 cm in diameter. Elution is performed first with chloroform (1 liter) and then a mixture of chloroform and methanol (95:5 by volume) (1 liter). These eluates are rejected. Elution is then performed with a mixture of chloroform and methanol (95:5 volume) (2 liters); the corresponding eluate is evaporated to dryness under reduced pressure (20 mm Hg; 2.7 kPa) at 40° C. 2-[4-(2-methylbenzyl)-1-piperazinyl]-4-phenyl-1-azaspiro[4.5-]deca-1,3,6,9-tetraen-8-one (5.8 g), m.p. 193° C., is thereby obtained.

3-(4-Methoxyphenylimino)-3-[4-(2-methylbenzyl)-1-piperazinyl]-1-propyne can be prepared by working as in Example 4, but starting with N-dichloromethylene-p-anisidine (20.4 g) dissolved in ethyl ether (200 cc), 1-(2-methylbenzyl)piperazine (38 g) dissolved in tetrahydofuran (400 cc) and a solution of phenylethynyllithium obtained by reacting a 1.6M solution (66 cc) of n-butyllithium dissolved in hexane with phenylacetylene (10.7 g) dissolved in tetrahydrofuran (200 cc). The maleate is prepared from 8.7 g of maleic acid. After recrystallization in ethanol (200 cc), 3-(4-methoxyphenylimino)-3-[4-(2-methylbenzyl)-1-piperazinyl]-1-phenyl-1-propyne maleate, m.p. 188° C., is obtained.

EXAMPLE 8

By working as in Example 5, but starting with 2-[4-(4-methylbenzyl)-1-piperazinyl]-4-phenyl-1-azaspiro[4.5-]deca-1,3,6,9-tetraen-8-one (34.8 g) and 1,2,4-trichlorobenzene (500 cc), 3-[4-(4-methylbenzyl)-1-piperazinyl]-1-phenyl-7H-pyrrolo[1,2-a]azepin-7-one (12.4 g), m.p. 143° C., is obtained after recrystallization in acetonitrile (150 cc).

2-[4-(4-Methylbenzyl)-1-piperazinyl]-4-phenyl-1-azaspiro[4.5]deca-1,3,6,9-tetraen-8-one can be prepared by working as in Example 4, but starting with 3-(4-methoxyphenylimino)-3-[4-(4-methylbenzyl)-1-piperazinyl]-1-phenyl-1-propyne (5.2 g) and concentrated sulphuric acid (25 cc). 2-[4-(4-Methylbenzyl)-1-piperazinyl]-4-phenyl-1-azaspiro[4.5]deca-1,3,6,9-tetraen-8-one (2.1 g), m.p. 135° C., is thereby obtained after recrystallization in a mixture of acetonitrile and isopropyl ether (50:50 by volume) (60 cc).

3-(4-Methoxyphenylimino)-3-[4-(4-methylbenzyl)-1-piperazinyl]-1-phenyl-1-propyne can be prepared by working as in Example 4, but starting with N-dichloromethylene-p-anisidine (41 g) dissolved in ethyl ether (200 cc), 1-(4-methylbenzyl)piperazine (76 g) dissolved in tetrahydrofuran (450 cc) and a solution of phenylethynyllithium obtained by reacting phenylacetylene (21.5 g) dissolved in tetrahydrofuran (400 cc) with a 1.6M solution (130 cc) of n-butyllithium in hexane. The residue thereby obtained is dissolved in boiling ethanol (400 cc). Maleic acid (37.3 g), dissolved in boiling ethanol (400 cc), is added to the solution. After the mixture is cooled to a temperature of about 20° C., the precipitate formed is separated by filtration and then recrystallized in ethanol (1600 cc). 3-(4-Methoxyphenylimino)-3-[4-(4-methylbenzyl)-1-piperazinyl]-1-phenyl-1-propyne maleate (67.7 g), m.p. 182° c., is thereby obtained.

EXAMPLE 9

By working as in Example 5, but starting with 2-(4-methyl-1-piperazinyl)-4-phenylthio-1-azaspiro[4.5-]deca-1,3,6,9-tetraen-8-one (3.2 g) and 1,2,4-trichlorobenzene (100 cc), 3-(4-methyl-1-piperazinyl)-1-phenylthio-7H-pyrrolo[1,2-a]azepin-7-one (0.9 g), m.p. 120° C., is obtained after recrystallization in isopropyl ether (20 cc).

2-(4-Methyl-1-piperazinyl)-4-phenylthio-1-azaspiro[4.5]deca-1,3,6,9-tetraen-8-one can be prepared by working as in Example 4, but starting with 3-(4-methyl-1-piperazinyl)-3-(4-methoxyphenylimino)-1-phenylthio-1-propyne (7 g) and concentrated sulphuric acid (50 cc). After recrystallization in a mixture of ethyl acetate and isopropyl ether (50:50 by volume) (80 cc), 2-(4-methyl-1-piperazinyl)-4-phenylthio-1-azaspiro[4.5]deca-1,3,6,9-tetraen-8-one (1.1 g), m.p. 142° C., is thereby obtained.

3-(4-Methoxyphenylimino)-3-(4-methyl-1-piperazinyl)-1-phenylthio-1-propyne can be prepared by working as in Example 4, but starting with N-dichloromethylene-p-anisidine (10.2 g) dissolved in ethyl ether (50 cc), 4-methylpiperazine (10 g) dissolved in tetrahydrofuran (50 cc) and a solution of phenylthioethynyllithium obtained by reacting phenylthioacetylene (6.7 g) dissolved in tetrahydrofuran (50 cc) with a 1.6M solution (31 cc) of n-butyllithium in hexane. The residue thereby obtained is dissolved in boiling ethanol (100 cc). Maleic acid (8.3 g), dissolved in boiling ethanol (150 cc), is added to this solution. After the mixture is cooled to a temperature of about 20° C., the precipitate formed is separated by filtration and recrystallized in ethanol (350 cc). 3-(4-Methoxyphenylimino)-3-(4-methyl-1-piperazinyl)-1-phenylthio-1-propyne (10.3 g), m.p. 160° C., is thereby obtained.

Phenylthioacetylene can be prepared according to the method described by R. C. Cookson and R. Gopalan, J. Chem. Soc. Chem. Comm., 924 (1978).

EXAMPLE 10

By working as in Example 5, but starting with 7-chloro-2-[4-(4-methylbenzyl)-1-piperazinyl]-4-phenyl-1-azaspiro[4.5]deca-1,3,6,9-tetraen-8-one (10.5 g) and 1,2,4-trichlorobenzene (200 cc), a residue is obtained which is redissolved in boiling acetonitrile (60 cc). Maleic acid (3.3 g), dissolved in boiling acetonitrile (60 cc), is added to this solution. After the mixture is cooled to a temperature of about 20° C., the solution obtained is evaporated to dryness under reduced pressure (20 mm Hg; 2.7 kPa) at 40° C. After recrystallization of the residue in a mixture of methyl ethyl ketone (50 cc) and isopropyl ether (10 cc), 6-chloro-3-[4-(4-methylbenzyl)-1-piperazinyl]-1-phenyl-7H-pyrrolo[1,2-a]azepin-7-one (2.3 g), m.p. 183° C., is obtained.

7-Chloro-2-[4-(4-methylbenzyl)-1-piperazinyl]-4-phenyl-1-azaspiro[4.5]deca-1,3,6,9-tetraen-8-one can be prepared by working as in Example 4, but starting with 3-(3-chloro-4-methoxyphenylimino)-3-[4-(4-methylbenzyl)-1-piperazinyl]-1-phenyl-1-propyne (31.6 g) and concentrated sulphuric acid (150 cc). After recrystallization of the residue in ethanol (220 cc), 7-chloro-2-[4-(4-methylbenzyl)-1-piperazinyl]-4-phenyl-1-azaspiro[4.5]deca-1,3,6,9-tetraen-8-one (7.3 g), m.p. 161° C., is obtained.

3-(3-Chloro-4-methoxyphenylimino)-3-[4-(4-methylbenzyl)-1-piperazinyl]-1-phenyl-1-propyne can be prepared by working as in Example 4, but starting with N-dichloromethylene-3-chloro-4-methoxyaniline (44.8 g) dissolved in ethyl ether (375 cc), 4-(4-methylbenzyl)-piperazine (71.5 g) dissolved in tetrahydrofuran (188 cc) and a solution of phenylethynyllithium obtained by reacting phenylacetylene (23.97 g) dissolved in tetrahydrofuran (470 cc) with a 1.6M solution (141 cc) of n-butyllithium in hexane. After recrystallization in acetonitrile (45 cc), 3-(3-chloro-4-methoxyphenylimino)-3-[4-(4-methylbenzyl)-1-piperazinyl]-1-phenyl-1-propyne (5 g), m.p. 113° c., is thereby obtained.

EXAMPLE 11

By working as in Example 5, but starting with 2-(4-benzyl-1-piperazinyl)-4-(4-methoxyphenyl)-1-azaspiro[4.5]deca-1,3,6,9-tetraen-8-one (13 g) and 1,2,4-trichlorobenzene (250 cc), 3-(4-benzyl-1-piperazinyl)-1-(4-methoxyphenyl)-7H-pyrrolo[1,2-a]azepin-7-one (8.7 g) m.p. 155° C., is obtained after recrystallization in acetonitrile (150 cc).

2-(4-Benzyl-1-piperazinyl)-4-(4-methoxyphenyl)-1-azaspiro[4.5]deca-1,3,6,9-tetraen-8-one can be prepared in the following manner: to a stirred solution of 3-(4-benzyl-1-piperazinyl)-1-(4-methoxyphenyl)-3-(4-methoxyphenylimino)-1-propyne (13 g) in acetic acid (60 cc), concentrated sulphuric acid (10 cc) is added in the course of 5 minutes at a temperature of about 15° C., and the mixture is left stirring for 48 hours at a temperature of about 20° C. The reaction mixture is then evaporated to dryness under reduced pressure (20 mm Hg; 2.7 kPa) at 40° C. The residue obtained is taken up with an 11N ammonia solution (40 cc) and the mxiture is extracted with methylene chloride (3×250 cc). The methylene chloride fractions are combined, washed with distilled water (2×100 cc), dried over anhydrous magnesium sulphate, filtered and evaporated to dryness under reduced pressure (20 mm Hg; 2.7 kPa) at 40° C. 2-(4-Benzyl-1-piperazinyl)-4-(4-methoxyphenyl)-1-azaspiro[4.5]deca-1,3,6,9-tetraen-8-one (13 g), m.p. 190° C., is thereby obtained.

3-(4-Benzyl-1-piperazinyl)-3-(4-methoxyphenylimino)-1-(4-methoxyphenyl)-1-propyne can be prepared in the following manner: to a solution of N-dichloromethylene-p-anisidine (41 g) in ethyl ether (450 cc), a solution of 4-benzylpiperazine (71 g) in tetrahydrofuran (550 cc) is added at a temperature of about 5° C. in the course of 20 minutes, and the mixture is stirred for 2 hours at a temperature of about 20° C. The insoluble material which has formed is separated by filtration. The solution thereby obtained is added in the course of 30 minutes at a temperature of about −65° C. to a solution of 2-(4-methoxyphenyl)ethynyllithium obtained by adding, in the course of 20 minutes at a temperature of about −70° C., a 1.6M solution (310 cc) of n-butyllithium in hexane to a solution of 4-methoxy-β,β-dibromostyrene (73 g) in tetrahydrofuran (750 cc), the temperature then being allowed to rise to about 20° C. and the mixture being stirred for a further 1 hour at this temperature.

The temperature of the reaction mixture is allowed to rise to about 20° C., and the mixture is stirred for 12 hours at this temperature; the reaction mixture is then poured onto crushed ice (1 kg). The aqueous solution is extracted with ethyl ether (1 liter) and then with methylene chloride (2×500 cc). The organic fractions are combined, washed with distilled water (250 cc), dried over anhydrous sodium sulphate, filtered and evaporated to dryness under reduced pressure (20 mm Hg; 2.7 kPa) at 40° C. The residue thereby obtained is stirred for 10 minutes at a temperature of about 20° C. with ethyl acetate (800 cc). The residue which was not dissolved is separated by filtration. 3-(4-Benzyl-1-piperazinyl)-3-(4-methoxyphenylimino)-1-(4-methoxyphenyl)-1-propyne (25 g), m.p. 161° C., is thereby obtained after recrystallization in acetonitrile (550 cc).

4-Methoxy-β,β-dibromostyrene can be prepared by the method described by H. J. Bestmann and K. Li, Chem. Ber., 115, 828 (1982).

EXAMPLE 12

By working as in Example 5, but starting with 2-(4-benzyl-1-piperazinyl)-4-(4-hydroxyphenyl)-1-azaspiro[4.5]deca-1,3,6,9-tetraen-8-one (3.8 g) and 1,2,4-trichlorobenzene (100 cc), 3-(4-benzyl-1-piperazinyl)-1-(4-hydroxyphenyl)-7H-pyrrolo[1,2-a]azepin-7-one (1.9 g), m.p. 186° C., is obtained after recrystallization in a mixture of acetonitrile and dimethylformamide (70:30 by volume) (30 cc).

2-(4-Benzyl-1-piperazinyl)-4-(4-hydroxyphenyl)-1-azaspiro[4.5]deca-1,3,6,9-tetraen-8-one can be obtained in the following manner: 2-(4-benzyl-1-piperazinyl)-4-(4-methoxyphenyl)-1-azaspiro[4.5]deca-1,3,6,9-tetraen-8-one (6.3 g) dissolved in acetic acid (150 cc) and a 48% strength solution of hydrobromic acid (100 cc) are heated for 12 hours to a temperature of about 100° C. After being cooled to a temperature of about 20° C., the solution is evaporated to dryness under reduced pressure (20 mm Hg; 2.7 kPa) at 40° C. Crushed ice (200 g) is added to the residue, followed by 11N aqueous ammonia solution (500 cc). The aqueous solution is washed with chloroform (2×300 cc). The organic fractions are combined, washed with distilled water (200 cc), dried over anhydrous sodium sulphate, filtered and evaporated to dryness under reduced pressure (20 mm Hg; 2.7 kPa) at 40° C. The residue obtained is dissolved in chloroform (200 cc) and the solution is poured into silica (120 g) contained in a column 3.2 cm in diameter. Elution is performed first with chloroform (1 liter) and the corresponding eluate is rejected. Elution is then performed with a mixture of chloroform and methanol (95:5 volume) (1 liter) and the corresponding eluate is evaporated to dryness under reduced pressure (20 mm Hg; 2.7 kPa) at 40° C. 2-(4-Benzyl-1-piperazinyl)-4-(4- hydroxyphenyl)-1-azaspiro[4.5]deca-1,3,6,9-tetraen-8-one (3.8 g) is thereby obtained in the form of a brown cake.

$R_f$=0.19 (thin layer chromatography on silica; eluant: chloroform/methanol, 90:10 by volume).

Mass spectrum: m/z=411 (M·+).

2-(4-Benzyl-1-piperazinyl)-4-(4-methoxyphenyl)-1-azaspiro[4.5]deca-1,3,6,9-tetraen-8-one can be prepared as described in Example 11.

EXAMPLE 13

By working as in Example 5, but starting with 2-(4-allyl-1-piperazinyl)-4-phenylthio-1-azaspiro[4.5]deca-1,3,6,9-tetraen-8-one (15.2 g) and 1,2,4-trichlorobenzene (150 cc), a residue is obtained which is redissolved in chlorofrom (300 cc). The solution obtained is poured into silica (300 g) contained in a column 4.2 cm in diameter. Elution is first performed with chloroform (1 liter) and this eluate is rejected. Elution is then performed with a mixture of chloroform and methanol (90:10 by volume) (3 liters) and the corresponding eluate is evaporated to dryness under reduced pressure (20 mm Hg; 2.7 kPa) at 40° C. The residue obtained is dissolved in acetone (15 cc). Oxalic acid (1.9 g), dissolved in acetone (15 cc), is added to the solution obtained. The precipitate formed is separated by filtration and washed with ethyl ether (10 cc). 3-(4-Allyl-1-piperazinyl)-1-phenylthio-7H-pyrrolo[1,2-a]azepin-7-one dioxalate (2.45 g), m.p. 225° C., is thereby obtained.

2-(4-Allyl-1-piperazinyl)-4-phenylthio-1-azaspiro[4.5-]deca-1,3,6,9-tetraen-8-one can be prepared by working as in Example 4, but starting with 3-(4-allyl-1-piperazinyl)-3-(4-methoxyphenylimino)-1-phenylthio-1-propyne (25 g) and concentrated sulphuric acid (125 cc). 2-(4-Allyl-1-piperazinyl)-4-phenylthio-1-azaspiro[4.5]deca-1,3,6,9-tetraen-8-one (15.2 g), m.p. 175° C., is thereby obtained.

3-(4-Allyl-1-piperazinyl)-3-(4-methoxyphenylimino)-1-phenylthio-1-propyne can be prepared by working as in Example 4, but starting with N-dichloromethylene-p-anisidine (54 g) dissolved in ethyl ether (500 cc), 4-allylpiperazine (67 g) dissolved in ethyl ether (450 cc) and a solution of phenylthioethynyllithium obtained by reacting phenylthioacetylene (34.4 g) dissolved in tetrahydrofuran (250 cc) with a 1.6M solution (154 cc) of n-butyllithium in hexane. After recrystallization in acetonitrile (150 cc), 3-(4-allyl-1-piperazinyl)-3-(4-methoxyphenylimino)-1-phenylthio-1-propyne (32 g), m.p. 75° C., is thereby obtained.

EXAMPLE 14

To a solution of 3-(1-piperazinyl)-1-phenyl-7H-pyrrolo[1,2-a]azepin-7-one (3 g) and 4-dimethylaminopyridine (1.46 g) in chloroform (100 cc), propargyl bromide (1.45 g) dissolved in chloroform (5 cc) is added. The solution is heated with stirring for 12 hours to a temperature of about 55° C. After being cooled to a temperature of about 20° C., the reaction mixture is evaporated to dryness under reduced pressure (20 mm Hg; 2.7 kPa) at 40° C., and the residue obtained is dissolved in methylene chloride (100 cc). This solution is poured into silica (80 g) contained in a column 2.7 cm in diameter. Elution is first performed with chloroform (200 cc); the corresponding eluate is rejected. Elution is then performed with a mixture of chloroform and methanol (95:5 by volume) (500 cc); the corresponding eluate is evaporated to dryness under reduced pressure (20 mm Hg; 2.7 kPa) at 40° C. The residue obtained is dissolved in acetonitrile (20 cc). Fumaric acid (690 mg), dissolved in boiling ethanol (5 cc), is added to this solution. After the mixture is cooled to a temperature of about 0° C., the precipitate which has formed is separated by filtration. After recrystallization in boiling acetonitrile (12 cc), 3-(4-propargyl-1-piperazinyl)-1-phenyl-7H-pyrrolo[1,2-a]azepin-7-one fumarate (0.40 g), m.p. 202° C., is obtained.

3-(1-Piperazinyl)-1-phenyl-7H-pyrrolo[1,2-a]azepin-7-one can be prepared as described in Example 2.

EXAMPLE 15

To a solution of 1-phenyl-3-[4-(2-tetrahydropyranyloxyethyl)-1-piperazinyl]-7H-pyrrolo[1,2-a]azepin-7-one (1.5 g) in chloroform (15 cc) and methanol (15 cc), 11.5M aqueous hydrochloric acid solution (1 cc) is added and the mixture is stirred at a temperature of about 20° C. for 12 hours. The solvents are evaporated off and the residue thereby obtained is dissolved in methylene chloride (50 cc). The solution is washed with 1N aqueous sodium hydroxide solution (25 cc) and twice with distilled water (50 cc in total), dried over anhydrous magnesium sulphate in the presence of decolorizing charcoal, filtered and evaporated to dryness under reduced pressure (20 mm Hg; 2.7 kPa) at 40° C. 3-[4-(2-Hydroxyethyl)-1-piperazinyl]-1-phenyl-7H-pyrrolo[1,2-a]azepin-7-one (0.28 g) is thereby obtained in the form of a pale yellow oil.

NMR spectrum (250 MHz, CDCl$_3$, δ in ppm, J in Hz):

2.7 : triplet, 2H: 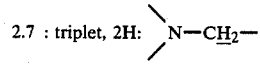

2.8 : singlet, 4H
3.10: triplet, 4H  } : piperazine —CH$_2$—

3.70: multiplet, 3H: —C$\underline{H}_2$OH 5.95: doublet of doublets: J = 11 and 2
6.15: doublet of doublets: J = 12.5 and 2  } 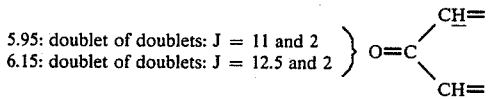

6.25: singlet, 1H: pyrrole —C$\underline{H}$=

7.30: doublet, 1H, J = 12.5 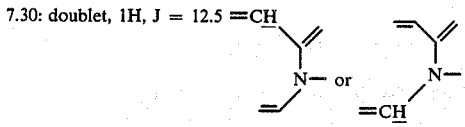

7.45: unresolved complex, 5H: aromatic protons 7.65: doublet, 1H, J = 11 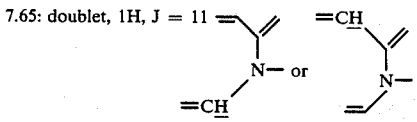

1-Phenyl-3-[4-(2-tetrahydropyranyloxyethyl)-1-piperazinyl]-7H-pyrrolo[1,2-a]azepin-7-one can be prepared by working as in Example 2, but starting with 1-phenyl-3-(1-piperazinyl)-7H-pyrrolo[1,2-a]azepin-7-one (6.8 g), 1-bromo-2-tetrahydropyranyloxyethane (5.12 g) and 4-dimethylaminopyridine (3 g) in chloroform (150 cc). After evaporation to dryness under reduced pressure (20 mm Hg; 2.7 kPa) at 40° C., the residue obtained is dissolved in chloroform (150 cc) and the solution is poured into silica (500 g) contained in a column 5 cm in diameter. Elution is first performed with chloroform (1 liter) and then with a mixture of chloroform and methanol (98:2 by volume) (1 liter); the corresponding eluates are rejected. Elution is then performed with a mixture of chloroform and methanol (96:4 by volume) (2 liters); the corresponding eluate is evaporated to dryness under reduced pressure (20 mm Hg; 2.7 kPa) at 40° C. 1-Phenyl-3-[4-(2-tetrahydropyranyloxyethyl)-1-piperazinyl]-7H-pyrrolo[1,2-a]azepin-7-one (1.5 g) is thereby obtained in the form of an orange oil, and this is employed as it is in the subsequent synthesis.

1-Bromo-2-tetrahydropyranyloxyethane can be prepared according to the method described by W. E. Parham and E. L. Anderson, J. Am. Chem. Soc., 70, 4187, (1948).

3-(1-Piperazinyl)-1-phenyl-7H-pyrrolo[1,2-a]azepin-7-one can be prepared as described in Example 2.

EXAMPLE 16

By working as in Example 5, but starting with 2-[4-(4-methylbenzyl)-1-homopiperazinyl]-4-phenyl-1-azaspiro[4.5]deca-1,3,6,9-tetraen-8-one (2.6 g) and 1,2,4-trichlorobenzene (55 cc), an oil (2.5 g) is obtained which is redissolved in ethyl acetate (10 cc). Maleic acid (0.70 g) is added to the solution obtained; the product which crystallizes is separated by filtration and washed with ethyl ether (25 cc). 3-[4-(4-Methylbenzyl)-1-homopiperazinyl]-1-phenyl-7H-pyrrolo[1,2-a]azepin-7-one maleate (2 g), m.p. 165° C., is thereby obtained.

2-[4-(4-Methylbenzyl)-1-homopiperazinyl]-4-phenyl-1-azaspiro[4.5]deca-1,3,6,9-tetraen-8-one can be prepared by working as in Example 4 but starting with 3-(4-methoxyphenylimino)-3-[4-(4-methylbenzyl)-1-homopiperazinyl]-1-phenyl-1-propyne (7 g) and concentrated sulphuric acid (35 cc). After recrystallization in a mixture of isopropyl ether and acetonitrile (50:50 by volume), 2-[4-(4-methylbenzyl)-1-homopiperazinyl]-4-phenyl-1-azaspiro[4.5]deca-1,3,6,9-tetraen-8-one (1.8 g), m.p. 122° C., is obtained.

3-(4-Methoxyphenylimino)-3-[4-(4-methylbenzyl)-1-homopiperazinyl]-1-phenyl-1-propyne can be prepared by working as in Example 4, but starting with N-dichloromethylene-p-anisidine (12 g) dissolved in ethyl ether (120 cc), 1-(4-methylbenzyl)homopiperazine (23.4 g) dissolved in tetrahydrofuran (25 cc) and a solution of phenylethynyllithium obtained by reacting phenylacetylene (6.2 g) dissolved in tetrahydrofuran (100 cc) with a 1.6M solution (38 cc) of n-butyllithium in hexane. After recrystallization in petroleum ether (50 cc), 3-(4-methoxyphenylimino)-3-[4-(4-methylbenzyl)-1-homopiperazinyl]-1-phenyl-1-propyne (4.8 g), m.p. 66° C., is obtained.

EXAMPLE 17

By working as in Example 5, but starting with a 4-(4-methoxyphenyl)-2-[4-(4-methylbenzyl)-1-piperazinyl]-1-azaspiro[4.5]deca-1,3,6,9-tetraen-8-one (3.9 g) and 1,2,4-trichlorobenzene (100 cc), 1-(4-methoxyphenyl)-3-[4-(4-methylbenzyl)-1-piperazinyl]-7H-pyrrolo[1,2-a]azepin-7-one (2.3 g), m.p. 153° C., is obtained after recrystallization in 2-butanone (30 cc).

4-(4-Methoxyphenyl)-2-[4-(4-methoxybenzyl)-1-piperazinyl]-1-azaspiro[4.5]deca-1,3,6,9-tetraen-8-one can be prepared as in Example 11, but starting with 1-(4-methoxyphenyl)-3-(4-methoxyphenylimino)-3-[4-(4-methylbenzyl)-1-piperazinyl]-1-propyne (5.1 g), acetic acid (50 cc) and concentrated sulphuric acid (2 cc). After recrystallization in isopropyl ether (30 cc), 4-(4-methoxyphenyl)-2-[4-(4-methoxybenzyl)-1-piperazinyl]-1-azaspiro[4.5]deca-1,3,6,9-tetraen-8-one (3.9 g), m.p. 142° C., is thereby obtained.

1-(4-Methoxyphenyl)-3-(4-methoxyphenylimino)-3-[4-(4-methylbenzyl)-1-piperazinyl]-1-propyne can be prepared as in Example 11, but starting with N-dichloromethylene-p-anisidine (4 g), 1-(4-methylbenzyl)piperazine (7.6 g), 1.6M solution (16 cc) of n-butyllithium in hexane and 4-methoxy-β,β-dibromostyrene (5.8 g). After recrystallization in acetonitrile (50 cc), 1-(4-methoxyphenyl)-3-(4-methoxyphenylimino)-3-[4-(4-methylbenzyl)-1-piperazinyl]-1-propyne (5.1 g), m.p. 107° C., is obtained.

EXAMPLE 18

By working as in Example 5, but starting with 4-(4-hydroxyphenyl)-2-[4-(4-methylbenzyl)-1-piperazinyl]-1-azaspiro[4.5]deca-1,3,6,9-tetraen-8-one (2.8 g) and 1,2,4-trichlorobenzene (80 cc), 1-(4-hydroxyphenyl)-3-[4-(4-methylbenzyl)-1-piperazinyl]-7H-pyrrolo[1,2-a]azepin-7-one (1.3 g), m.p. 206° C., is obtained after recrystallization in 2-butanone (40 cc).

4-(4-Hydroxyphenyl)-2-[4-(4-methylbenzyl)-1-piperazinyl]-1-azaspiro[4.5]deca-1,3,6,9-tetraen-8-one can be obtained in the following manner: 1-(4-methoxyphenyl)-2-[4-(4-methylbenzyl)-1-piperazinyl]-1-azaspiro[4.5]deca-1,3,6,9-tetraen-8-one (8.1 g) dissolved in acetic acid (150 cc) and 48% strength hydrobromic acid solution (80 cc) are heated for 8 hours to a temperature of about 100° C. After the mixture is cooled to a temperature of about 20° C., the solution is evaporated to dryness under reduced pressure (20 mm Hg; 2.7 kPa) at 40° C. Crushed ice (200 g) is added to the residue, followed by 11N aqueous ammonia solution (110 cc), The aqueous solution is extracted 4 times with chloroform (400 cc in total). The organic fractions are combined, washed with distilled water (50 cc), dried over anhydrous magnesium sulphate, filtered and evaporated to dryness under reduced pressure (20 mm Hg; 2.7 kPa) at 40° C. The residue obtained is dissolved in methylene chloride (200 cc) and the solution is poured into silica (120 g) contained in a column 3.2 cm in diameter. Elution is first performed with methylene chloride (1.6 liters) and the corresponding eluate is rejected. Elution is then performed with a mixture of methylene chloride and methanol (95:5 by volume) (1.4 liter) and the corresponding eluate is evaporated to dryness under reduced pressure (20 mm Hg; 2.7 kPa) at 40° C. 4-(4-hydroxyphenyl)-2-[4-(4-methylbenzyl)-1-piperazinyl]-1-azaspiro[4.5]deca-1,3,6,9-tetraen-8-one (2.8 g) is thereby obtained in the form of a crystallized solid, m.p. 140° C.

1-(4-Methoxyphenyl)-2-[4-(4-methylbenzyl)-1-piperazinyl]-1-azaspiro[4.5]deca-1,3,6,9-tetraen-8-one can be prepared as in Example 17.

EXAMPLE 19

A solution of 4-(2-methoxyphenyl)-2-[4-(4-methylbenzyl)-1-piperazinyl]-1-azaspiro[4.5]deca-1,3,6,9-tetraen-8-one (2.8 g) in 1,2,4-trichlorobenzene (80 cc) is heated for 4 hours at a temperature of about 210° C. After evaporation to dryness under reduced pressure (1 mm Hg; 0.13 kPa) at 40° C., the residue obtained is dissolved in methylene chloride (50 cc) and the solution is poured into silica (60 g) contained in a column 2 cm in diameter. Elution is first performed with a mixture of methylene chloride and methanol (99:1 by volume) (200 cc); the corresponding eluates are rejected. Eluation is then performed with a mixture of methylene chloride and methanol (99:1 by volume) (450 cc) and the corresponding eluate is evaporated to dryness under reduced pressure (20 mm Hg; 2.7 kPa) at 40° C. After recrystallization of the residue in acetonitrile (75 cc), 1-(2-methoxyphenyl)-3-[4-(4-methylbenzyl)-1-piperazinyl]-7H-pyrrolo[1,2-a]azepin-7-one (1.8 g), m.p. 186° C., is obtained.

4-(2-Methoxyphenyl)-2-[4-(4-methylbenzyl)-1-piperazinyl]-1-azaspiro[4.5]deca-1,3,6,9-tetraen-8-one can be prepared by working as in Example 11, but starting with a stirred solution of 1-(2-methoxyphenyl)-3-(4-methoxyphenylimino)-3-[4-(4-methylbenzyl)-1-piperazinyl]propyne (4.6 g) and acetic acid (15 cc) to which sulphuric acid (25 cc) has been added. The mixture is left stirring for 30 minutes at room temperature. After trituration in isopropyl ether, 2-[4-(4-methylbenzyl)-1-piperazinyl]-4-(2-methoxyphenyl)-1-azaspiro[4.5-]deca-1,3,6,9-tetraen-8-one (2.8 g), m.p. 147° C., is obtained.

1-(2-Methoxyphenyl)-3-(4-methoxyphenylimino)-3-[4-(4-methylbenzyl)-1-piperazinyl]propyne can be prepared by working as in Example 11 but starting with a solution of N-dichloromethylene-p-anisidine (20.6 g) in ethyl ether (200 cc) to which a solution of 4-(4-methylbenzyl)piperazine (38.4 g) in tetrahydrofuran (150 cc) is added. The solution obtained after filtration is added in the course of 30 minutes at a temperature of about −70° C. to a solution of 2-(2-methoxyphenyl)ethynyllithium obtained by adding, in the course of 20 minutes, at a temperature of about −70° C., a 1.6M solution (126 cc) of butyllithium in hexane to a solution of 2-methoxy-β,β-dibromostyrene (29.5 g) in tetrahydrofuran (300 cc). 1-(2-Methoxyphenyl)-3-(4-methoxyphenylimino)-3-[4-(4-methylbenzyl)-1-piperazinyl]propyne (30.6 g), m.p. 83° C., is thereby obtained.

EXAMPLE 20

A solution of 2-[4-(4-ethoxycarbonylbenzyl)-1-piperazinyl]-4-phenyl-1-azaspiro[4.5]deca-1,3,6,9-tetraen-8-one (12.4 g) in 1,2,4-trichlorobenzene (250 cc) is heated for 11 hours to a temperature of about 210° C. After evaporation to dryness under reduced pressure (1 mm Hg; 0.13 kPa) at 40° C., the residue obtained is dissolved in methylene chloride (250 cc) and the solution is poured into silica (400 g) contained in a column 6 cm in diameter. Elution is first performed with methylene chloride (2 liters) and the corresponding eluates are rejected. Elution is then performed with a mixture of methylene chloride and methanol (99:1 by volume) (5 liters) and the corresponding eluate is evaporated to dryness under reduced pressure (20 mm Hg; 2.7 kPa) at 40° C. After recrystallization of the residue in ethanol (120 cc), 3-[4-(4-ethoxycarbonylbenzyl)-1-piperazinyl]-1-phenyl-7H-pyrrolo[1,2-a]azepin-7-one (5.7 g), m.p. 129° C., is obtained.

2-[4-(4-Ethoxycarbonylbenzyl)-1-piperazinyl]-4-phenyl-1-azaspiro[4.5]deca-1,3,6,9-tetraen-8-one can be prepared by working as in Example 11, but starting with sulphuric acid (135 cc) and a stirred solution of 3-[4-(4-ethoxycarbonylbenzyl)-1-piperazinyl]-3-(4-methoxyphenylimino)-1-phenylpropyne in acetic acid (80 cc). After trituration in isopropyl ether, 2-[4-(4-ethoxycarbonylbenzyl)-1-piperazinyl]-4-phenyl-1-azaspiro[4.5-]deca-1,3,6,9-tetraen-8-one (12.4 g), m.p. 199° C., is obtained.

3-[4-(4-Ethoxycarbonylbenzyl)-1-piperazinyl]-3-(4-methoxyphenylimino)-1-phenylpropyne can be prepared in the following manner: to a solution of N-dichloromethylene-p-anisidine (31.4 g) in tetrahydrofuran (200 cc) under an atmosphere of nitrogen, a solution of (4-ethoxycarbonylbenzyl)piperazine (38.2 g) in tetrahydrofuran (250 cc) is added at a temperature of about 15° C. in the course of 15 minutes, and stirring is continued for a further 1 hour at a temperature of about 20° C. The precipitate which has formed is separated by filtration. The solution thereby obtained is added in the course of 30 minutes at a temperature of about −70° C. to a solution of phenylethynyllithium in tetrahydrofuran (200 cc), obtained by reacting, at a temperature of about −70° C., phenylacetylene (64.1 g) dissolved in tetrahydrofuran (200 cc) with a 1.6M solution (385 cc) of n-butyllithium in hexane. The mixture is left to react for 1 hour 30 minutes at −70° C. and then for 2 hours at −20° C., and is then allowed to warm to a temperature of about 20° C. The mixture is evaporated to dryness under reduced pressure (20 mm Hg; 2.7 kPa) at 40° C.; the residue obtained is taken up in distilled water (700 cc) and extracted with methylene chloride (4×500 cc). The organic fractions are combined and washed with distilled water (500 cc), dried over anhydrous magnesium sulphate, filtered and then evaporated to dryness under reduced pressure (20 mm Hg; 2.7 kPa) at 40° C. The residue obtained is dissolved in methylene chloride (200 cc) and the solution is poured into silica (2 kg) contained in a column 8 cm in diameter. Elution is first performed with methylene chloride (1 liter) and then with a mixture of methylene chloride and methanol (99:1 by volume) (1 liter); the corresponding eluates are rejected. Elution is then performed with a mixture of methylene chloride and methanol (99:1 by volume) (15 liters), and the corresponding eluate is evaporated to dryness under reduced pressure (20 mm Hg; 2.7 kPa) at 40° C. 3-[4-(4-Ethoxycarbonylbenzyl)-1-piperazinyl]-3-(4-methoxyphenylimino)-1-phenylpropyne (21.4 g) is thereby obtained in the form of a brown oil.

$R_f$=0.36 (thin layer chromatography on silica gel: eluant: methylene chloride/methanol, 96.4 by volume).

EXAMPLE 21

To a stirred suspension of 3-[4-(4-ethoxycarbonyl benzyl)-1-piperazinyl]-1-phenyl-7H-pyrrolo[1,2-a]azepin-7-one (1.2 g), prepared as described in Example 20, and ethyl alcohol (30 cc) under an atmosphere of nitrogen, a solution of potassium hydroxide (0.2 g) in distilled water (3 cc) is added at a temperature of about 20° C. in the course of 5 minutes. The reaction mixture is then heated to 60° C. for 4 hours. After the solution is cooled, 1N aqueous potassium hydroxide solution (10 cc) is added and the mixture is washed 3 times with methylene chloride (150 cc in total). The organic phases are combined, dried over anhydrous magnesium sulphate, filtered and evaporated to dryness under reduced pressure (20 mm Hg; 2.7 kPa) at 40° C. The residue is dissolved in methylene chloride (5 cc) and the solution is poured into silica (40 g) contained in a column 1 cm in diameter. Elution is first performed with a mixture of cyclohexane and ethyl acetate (50:50 by volume) (2.5 liters and the corresponding eluate is rejected. Elution is then performed with methanol (1 liter and the corresponding eluate is evaporated to dryness under reduced pressure (20 mm Hg; 2.7 kPa) at 40° C. After recrystallization in 2-methyl-2-butanol, 3-[4-(4-carboxybenzyl)-1- piperazinyl]-1-phenyl-7H-pyrrolo[1,2-a]azepin-7-one (0.6 g) is obtained in the form of its potassium salt.

$R_f = 0.30$ (thin layer chromatography on silica; eluant: chloroform/methanol, 98:2 by volume).

The present invention also provides pharmaceutical compositions which comprise a compound of formula (I), in free form or in the form of an addition salt with a pharmaceutically acceptable acid or base, in combination with one or more compatible pharmaceutically acceptable diluents or adjuvants. Such compositions can be used orally, parenterally or rectally.

As solid compositions for oral administration, tablets, pills, powders (in particular in gelatin capsules or in wafer capsules) or granules can be used. In these compositions, the active product according to the invention is mixed with one or more inert diluents such as starch, cellulose, sucrose, lactose or silica. These compositions can also contain substances other than diluents, for example one or more lubricants such as magnesium stearate or talc, a colouring, a coating (dragees) or a lacquer.

As liquid compositions for oral administration, pharmaceutically acceptable solutions, suspensions, emulsions, syrups and elixirs can be used, containing inert diluents such as water, ethanol, glycerol, vegetable oils or liquid paraffin. These compositions can also contain substances other than diluents, for example wetting agents, sweeteners, thickeners, flavourings or stabilizers.

The sterile compositions for parenteral administration can preferably be aqueous of non-aqueous solutions, or suspensions or emulsions. As a solvent or vehicle, water, propylene glycol, a polyethylene glycol, vegetable oils, especially olive oil, injectable organic esters e.g. ethyl oleate, or other suitable organic solvents can be employed. These compositions can also contain adjuvants, especially wetting agents, tonicity agents, emulsifiers, dispersants and stabilizers. The sterilization can be carried out in several ways, for example by aseptic filtration, by incorporating sterilizing agents in the composition, by irradiation or by heating. They can also be prepared in the form of sterile solid compositions which can be dissolved at the time of use in an injectable sterile medium.

The compositions for rectal administration are suppositories or rectal capsules which contain, in addition to the active product, excipients such as cocoa butter, semi-synthetic glycerides or polyethylene glycols.

In human therapy, the products according to the invention are especially useful in the treatment of disorders of the psyche, and more especially psychoses such as schizophrenia or delirium. The dosages depend on the effects sought and the length of treatment; they are generally between 25 and 250 mg per day orally for an adult, taken in one or more doses.

In general, the doctor will determine the dosage regimen which he judges to be the most suitable in accordance with the age, weight and all other factors specific to the subject to be treated.

The examples which follow, which are given without implied limitation, illustrate some compositions according to the invention.

EXAMPLE A

Tablets containing a 25-mg dose of active product and having the following composition are prepared according to the usual technique:

| | |
|---|---|
| 3-[4-(4-methylbenzyl)-1-piperazinyl]-1-phenyl-7H—pyrrolo[1,2-a]azepin-7-one | 25 mg |
| starch | 60 mg |
| lactose | 50 mg |
| magnesium stearate | 2 mg |

EXAMPLE B

An injectable solution containing 25 mg of active product and having the following composition is prepared:

| | |
|---|---|
| 3-[4-(4-methylbenzyl)-1-piperazinyl]-1-phenyl-7H—pyrrolo[1,2-a]azepin-7-one | 25 mg |
| 0.1 N aqueous solution of methanesulphonic acid | 1.23 cc |
| injectable solution q.s. | 12.5 cc |

We claim:

1. A pyrrolo[1,2-a]azepinone of the formula:

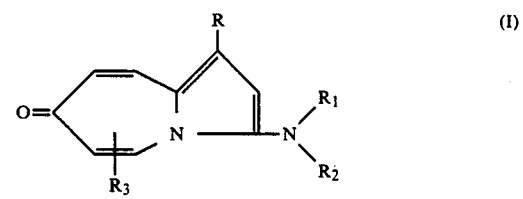

in which $R_3$ denotes hydrogen or halogen, and either (A) R denotes phenylthio in which the phenyl is unsubstituted or monosubstituted by halogen, hydroxy, alkyl, alkyloxy or alkylthio, and $R_1$ and $R_2$ form, together with the nitrogen atom to which they are linked, 1-piperazinyl substituted by alkyl, alkenyl of 2 to 4 carbon atoms, or benzyl, the phenyl portion of the said benzyl being unsubstituted or monosubstituted by halogen, alkyl, alkyloxy, alkylthio, trifluoromethyl, carboxy, carboxyalkyl, alkyloxycarbonyl, alkyloxycarbonylalkyl, hydroxyalkyl, or alkylcarbonyloxyalkyl in which the alkylcarbonyl portion contains 2 to 18 carbon atoms in a straight or branched chain, or (B) R denotes phenyl or phenyl monosubstituted by halogen; hydroxy, alkyl, alkyloxy or alkylthio groups, and $R_1$ and $R_2$ form, together with the nitrogen atom to which they are linked, a piperazino or homopiperazino ring monosubstituted by hydroxyalkyl in which the alkyl contains 2 to 4 atoms, alkenyl of 2 to 4 carbon atoms, alkynyl of 2 to 4 carbon atoms, or a benzyl group in which the phenyl portion is unsubstituted or monosubstituted by halogen, alkyl, alkyloxy, alkylthio, cyano, trifluoromethyl, carboxy, carboxyalkyl, alkyloxycarbonyl, alkyloxycarbonylalkyl, hydroxyalkyl, or alkylcarbonyloxyalkyl in which the alkylcarbonyl portion contains 2 to 18 carbon atoms in a straight or branched chain, the aforesaid alkyl groups and alkyl portions containing, except where otherwise stated, 1 to 4 carbon atoms each in a straight or branched chain, and the pharmaceutically acceptable salts thereof.

2. A pyrrolo[1,2-a]azepinone as claimed in claim 1, in which $R_3$ denotes hydrogen or halogen and either (A) R denotes phenylthio and $R_1$ and $R_2$ form, together with the nitrogen atom to which they are linked, 1-piperazinyl substituted by alkyl, alkenyl of 2 to 4 carbon atoms, or benzyl in which the phenyl portion is unsubstituted or substituted by halogen, alkyl, alkyloxy, alkylthio, trifluoromethyl, carboxy or carboxyalkyl, or (B) R denotes phenyl or phenyl substituted by halogen, hydroxy, alkyl, alkyloxy or alkylthio groups and $R_1$ and $R_2$ form, together with the nitrogen atom to which they are linked, a piperazino or homopiperazino ring substituted by hydroxyalkyl in which the alkyl contains 2 to 4 carbon atoms, alkenyl of 2 to 4 carbon atoms, alkynyl of 2 to 4 carbon atoms, or a benzyl group in which the phenyl portion is unsubstituted or substituted by halogen, alkyl, cyano, trifluoromethyl, carboxy, carboxyalkyl, alkyloxycarbonyl, hydroxyalkyl, or alkylcarbonyloxyalkyl in which the alkylcarbonyl portion contains 2 to 18 carbon atoms in a straight or branched chain, and the pharmaceutically acceptable salts thereof.

3. A pyrrolo[1,2-a]azepinone as claimed in claim 1, in which $R_3$ denotes hydrogen or halogen and either (A) R denotes phenylthio and $R_1$ and $R_2$ form, together with the nitrogen atom to which they are linked, 1-piperazinyl substituted by alkyl or by alkenyl of 2 to 4 carbon atoms, or (B) R denotes phenyl or phenyl substituted by hydroxy, alkyl or alkyloxy and $R_1$ and $R_2$ form, together with the nitrogen atom to which they are linked, a piperazino or homopiperazino ring substituted by hyroxyalkyl in which the alkyl contains 2 to 4 carbon atoms, alkenyl of 2 to 4 carbon atoms, alkynyl of 2 to 4 carbon atoms, or benzyl in which the phenyl portion is unsubstituted or substituted by halogen, alkyl, cyano, trifluoromethyl, carboxy or alkyloxycarbonyl group, and the pharmaceutically acceptable salts thereof.

4. A pyrrolo[1,2a]azepinone as claimed in claim 1, which is 3-[4-(4-methylbenzyl)-1-piperazinyl]-1-phenyl-7H-pyrrolo[1,2-a]azepin-7-one and the pharmaceutically acceptable salts thereof.

5. A pyrrolo[1,2-a]azepinone as claimed in claim 1, which is 1-(4-hydroxyphenyl)-3-[4-(4-methylbenzyl)-1-piperazinyl]-7H-pyrrolo[1,2-a]azepin-7-one and the pharmaceutically acceptable salts thereof.

6. A pyrrolo[1,2,-a]azepinone as claimed in claim 1, which is 3-[4-(4-methylbenzyl)-1-piperazinyl]-1-(4-methoxyphenyl)-7H-pyrrolo[1,2-a]azepin-7-one and the pharmaceutically acceptable salts thereof.

7. A pyrrolo[1,2-a]azepinone as claimed in claim 1, which is 3-(4-benzyl-1-piperazinyl)-1-(4-hydroxyphenyl)-7H-pyrrolo[1,2-a]azepin-7-one and the pharmaceutically acceptable salts thereof.

8. A pyrrolo[1,2-a]azepinone as claimed in claim 1, which is 3-(4-benzyl-1-piperazinyl)-1-(4-methoxyphenyl)-7H-pyrrolo[1,2-a]azepin-7-one and the pharmaceutically acceptable salts thereof.

9. A pyrrolo[1,2-a]azepinone as claimed in claim 1, which is 3-[4-(4-fluorobenzyl)-1-piperazinyl]-1-phenyl-7H-pyrrolo[1,2-a]azepin-7-one and the pharmaceutically acceptable salts thereof.

10. A pyrrolo[1,2-a]azepinone as claimed in claim 1, which is 3-(4-benzyl-1-piperazinyl)-1-phenyl-7H-pyrrolo[1,2-a]azepin-7-one and the pharmaceutically acceptable salts thereof.

11. A pyrrolo[1,2-a]azepinone as claimed in claim 1, which is 3-[4-(3-trifluoromethylbenzyl)-1-piperazinyl]-1-phenyl-7H-pyrrolo[1,2-a]azepin-7-one and the pharmaceutically acceptable salts thereof.

12. A pyrrolo[1,2-a]azepinone as claimed in claim 1, which is 3-[4-(4-methylbenzyl)-1-piperazinyl]-1-(2-methoxyphenyl)-7H-pyrrolo[1,2-a]azepin-7-one and the pharmaceutically acceptable salts thereof.

13. A pyrrolo[1,2-a]azepinone as claimed in claim 1, which is 3-(4-methyl-1-piperazinyl)-1-phenylthio-7H-pyrrolo[1,2-a]azepin-7-one and the pharmaceutically acceptable salts thereof.

14. A pyrrolo[1,2-a]azepinone as claimed in claim 1, which is 3-(4-allyl-1-piperazinyl)-1-phenylthio-7H-pyrrolo[1,2-a]azepin-7-one and the pharmaceutically acceptable salts thereof.

15. A pyrrolo[1,2-a]azepinone as claimed in claim 1, which is 3-[4-(4-carboxybenzyl)-1-piperazinyl]-1-phenyl-7H-pyrrolo[1,2-a]azepin-7-one and the pharmaceutically acceptable salts thereof.

16. A pharmaceutical composition useful for treating a psychosis which contains an effective amount of a pyrrolo[1,2-a]azepinone according to claim 1, or a pharmaceutically acceptable salt thereof in combination with one or more compatible, pharmaceutically acceptable diluents or adjuvants.

17. A method of treating psychoses which comprises administering to a patient suffering therefrom or liable thereto an effective amount of a pyrrolo[1,2-a]azepinone according to claim 1, or of a pharmaceutically acceptable salt thereof.

* * * * *